(12) United States Patent
Schmenger et al.

(10) Patent No.: US 7,648,535 B2
(45) Date of Patent: Jan. 19, 2010

(54) AGENT FOR COLORING KERATIN FIBRES

(75) Inventors: Juergen Schmenger, Weiterstadt (DE); Petra Braun, Muenster (DE); Jolanthe Kujawa, Darmstadt (DE); Martina Glattefelder, Heddesheim (DE); Anne Entzminger, Griesheim (DE); Anette Sallwey, Griesheim (DE); Herbert Deutz, Woodland Hills, CA (US)

(73) Assignee: Wella AG, Darmstadt (DE)

( * ) Notice: Subject to any disclaimer, the term of this patent is extended or adjusted under 35 U.S.C. 154(b) by 156 days.

(21) Appl. No.: 10/570,365

(22) PCT Filed: Jul. 6, 2004

(86) PCT No.: PCT/EP2004/007366

§ 371 (c)(1),
(2), (4) Date: Mar. 2, 2006

(87) PCT Pub. No.: WO2005/032502

PCT Pub. Date: Apr. 14, 2005

(65) Prior Publication Data

US 2007/0000069 A1    Jan. 4, 2007

(30) Foreign Application Priority Data

Sep. 4, 2003    (DE) ................................ 103 40 695

(51) Int. Cl.
*A61Q 5/10*    (2006.01)

(52) U.S. Cl. ...................... 8/405; 8/406; 8/414; 8/435; 8/455; 8/667

(58) Field of Classification Search .................... 8/405, 8/406, 414, 435, 455, 667
See application file for complete search history.

(56) References Cited

U.S. PATENT DOCUMENTS

| 5,350,424 A | * | 9/1994 | Shansky | ........................ 8/406 |
| 5,891,200 A | * | 4/1999 | Lim et al. | ...................... 8/426 |
| 5,961,664 A | * | 10/1999 | Anderson | ....................... 8/405 |

FOREIGN PATENT DOCUMENTS

| DE | 199 44 527 A1 | 3/2001 |
| EP | 0 782 845 A1 | 7/1997 |
| EP | 1 166 748 | 1/2002 |

OTHER PUBLICATIONS

E. Sagarin: "Cosmetics, Science and Technology" NY 1957, pp. 503-507.
H. Janistyn: "Handbuch Der Kosmetika Und . . . ", Band 3, 1973, pp. 388-397.
Schrader: "Grundlagen Und Rezepturen Der Kosmetika" 2. Auflage 1989, pp. 782-815.

* cited by examiner

*Primary Examiner*—Eisa B Elhilo
(74) *Attorney, Agent, or Firm*—Michael J. Striker

(57) ABSTRACT

The agent for coloring keratin fibers is free of chemical oxidants, is in the form of an aqueous or aqueous-alcoholic dye-containing preparation, and contains a combination of oxidation dyes and at least three direct dyes. The agent is characterized by a quantitative ratio of oxidation dyes to direct dyes equal to 5:1 to 0.5:1. A method of dyeing hair is described in which the agent is applied to hair and allowed to act on the hair for an acting time of 5 to 60 minutes without addition of chemical oxidants, so that air oxidation provides a uniform and stable coloration of the hair.

16 Claims, No Drawings dye # AGENT FOR COLORING KERATIN FIBRES

CROSS-REFERENCE

This is the US National Stage of PCT/EP 2004/007366, filed on Jul. 6, 2004 in Europe.

BACKGROUND OF THE INVENTION

1. The Field of the Invention

The present invention relates to compositions for coloring keratin fibers, particularly human hair, based on a developer-coupler combination and direct dyes which compositions make it possible to impart to the fibers a lasting coloration without the addition of an oxidant (comparable to the stability of semipermanent colors) while at the same time causing only minor damage to the fibers (comparable to temporary hair dyes).

2. The Related Art

In the field of keratin fiber coloring, particularly hair coloring, oxidation dyes have attained substantial importance. The coloration is formed by reaction of certain developers with certain couplers in the presence of a suitable oxidant. For very gentle uses, however, the need exists for colorants which in the presence of atmospheric oxygen give lasting colorations even without the addition of an oxidant.

It is known from EP 1 166 748 A2 that the combination of oxidation dyes and optionally direct dyes can be used for hair dyeing without the addition of a chemical oxidant. Constant coloring results (namely a coloration that is the same immediately after the use as well as days or weeks thereafter) are not possible with the agents described in that document.

SUMMARY OF THE INVENTION

The purpose of the present invention therefore is to provide an agent which upon air oxidation does not develop the coloration only after days, but does so immediately after application giving a uniform coloration which remains virtually constant over a period of up to 20 hair washings.

Surprisingly, we have now found that by use of a special combination of oxidation dyes and direct dyes, the combination containing at least three direct dyes and the quantitative ratio of oxidation dyes to direct dyes being 5:1 to 0.5:1, it is possible to obtain outstanding coloring results characterized by a natural luster and a long-lasting uniform coloration without the original coloration undergoing a color change. The agent of the invention colors the hair in very gentle manner (comparable to the conventionally used readily washed out tinting agents) so that the hair remains practically undamaged. The object of the invention provides a constant coloration which lasts over a period of up to 20 washings of the colored hair.

The object of the invention therefore is an agent for coloring keratin fibers, particularly human hair, which is free of chemical oxidants and is characterized in that it is in the form of an aqueous or aqueous-alcoholic preparation and contains a combination of oxidation dyes (developers, couplers) and direct dyes, said combination containing at least three direct dyes, and that the quantitative ratio of oxidation dyes to direct dyes equals 5:1 to 0.5:1.

DESCRIPTION OF THE PREFERRED EMBODIMENTS

Suitable oxidation dye precursors are, for example, the following developers and couplers and self-coupling compounds:

(i) Developers: 1,4-diaminobenzene(p-phenylenediamine), 1,4-diamino-2-methylbenzene (p-toluylenediamine), 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)-benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)benzene, 2-[(2-acetylamino)ethoxy]-1,4-diaminobenzene, 4-phenylaminoaniline, 4-dimethylaminoaniline, 4-diethylaminoaniline, 4-dipropylaminoaniline, 4-[ethyl(2-hydroxyethyl)amino]aniline, 4-[di(2-hydroxyethyl)amino]aniline, 4-[di(2-hydroxyethyl)amino-2-methylaniline, 4-[(2-methoxyethyl)amino]aniline, 4-[(3-hydroxypropyl)amino]aniline, 4-[(2,3-dihydroxypropyl)amino]aniline, 1,4-diamino-2-(2-hydroxyethyl)benzene, 1,4-diamino-2-(1-methylethyl)benzene, 1,3-bis[(4-aminophenyl)(2-hydroxyethyl)amino]-2-propanol, 1,4-bis[(4-aminophenyl)amino]butane, 1,8-bis(2,5-diaminophenoxy)-3,6-dioxaoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxyethyl)amino]methylphenol, 4-amino-2-methylphenol, 4-amino-2-(methoxymethyl)phenol, 4-amino-2-(2-hydroxyethyl)phenol, 5-amino-salicylic acid, 2,5-diaminopyridine, 2,4,5,6-tetraminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 2-aminophenol, 2-amino-6-methylphenol and 2-amino-5-methylphenol, alone or in admixture with one another.

(ii) Couplers: N-(3-Dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxy-pyridine, 1,3-diaminobenzene, 2,4-diamino-1-(2-hydroxyethoxy)benzene, 1,3-diamino-4-(2,3-dihydroxypropoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxy-benzene, 2,6-bis(2-hydroxyethyl)aminotoluene, 4-hydroxyindole, 3-dimethylaminophenol, 3-dieth-ylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlo-rophenol, 3-amino-2-methylphenol, 3-amino-2-chloro-6-methylphenol, 3-aminophenol, 2-[(3-hydroxyphenyl)amino]

acetamide, 5-[(2-hydroxyethyl)amino]-4-methoxy-2-methylphenol, 5[(2-hydroxyethyl)amino]-2-methylphenol, 3[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxol, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione, alone or in admixture with one another.

(iii) Self-coupling compounds: 2-amino-5-methylphenol, 2-amino-6-methylphenol, 2-amino-6-ethoxyphenol or 2-propylamino-5-aminopyridine.

Among the afore-indicated oxidation dyes, the following compounds, alone or in combination with one another, are particularly preferred:

2,5-diaminotoluene, 2,4-diaminophenoxyethanol, resorcinol, 2-methylresorcinol, m-aminophenol, 4-amino-3-methylphenol, 4-amino-2-hydroxytoluene, 6-amino-3-methylphenol, 2-amino-4-hydroxyethylaminoanisole, 1-naphthol, hydroxyethyl-3,4-methylenedioxyaniline, 2,5-diaminophenylethanol, N,N-bis(2-hydroxyethyl)-p-phenylenediamine, phenylmethylpyrazolone, 1-hydroxyethyl-4,5-diaminopyrazole and 2-amino-6-chloro-4-nitrophenol or the salts thereof.

The total amount of oxidation dye precursors contained in the agent of the invention is about 0.01 to 12 weight percent and particularly about 0.1 to 7 weight percent. Particularly preferred dyes are listed in Table 1.

Suitable direct dyes are all common natural and/or synthetic direct dyes, for example the vegetable dyes such as henna or indigo, triphenylmethane dyes, aromatic nitro dyes, azo dyes, quinone dyes and cationic or anionic dyes.

Suitable synthetic dyes are, for example:
1,4-bis[(2-hydroxyethyl)amino]-2-nitrobenzene, 1-(2-hydroxyethyl)amino-2-nitro-4-[di(2-hydroxyethyl)amino]benzene (HC Blue No. 2), 1-amino-3-meth-yl-4-[(2-hydroxyethyl)amino]-6-nitrobenzene (HC Violet No. 1), 4-[ethyl-(2-hydroxyethyl)amino]-1-[(2-hydroxyethyl)amino]-2-nitrobenzene hydrochloride (HC Blue No. 12), 4-[di(2-hydro-xyethyl)amino]-1-[(2-methoxyethyl)amino]-2-nitrobenzene (HC Blue No. 11), 1-[(2,3-dihydroxy-propyl)amino]-4-[methyl-(2-hydroxyethyl)amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene (HC Violet No. 2), 1-meth-ylamino-4-[methyl-(2,3-dihydroxypropyl)amino]-2-nitrobenzene (HC Blue No. 6), 2-[(4-amino-2-nitrophenyl)amino]-5-dimethylaminobenzoic acid (HC Blue No. 13), 1-amino-4-[(2-hydroxy-ethyl)amino]-2-nitrobenzene (HC Red No. 7), 2-amino-4,6-dinitrophenol, 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)-amino]benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 1,2,3,4-tetrahydro-6-nitroquinoxaline, 7-amino-3,4-dihydro-6-nitro-2H-1,4-benzoxazine, (HC Red. No. 14), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-(2-hydroxyethoxy)-3-methylamino-4-nitrobenzene, 2,3-(dihydroxypropoxy)-3-methylamino-4-nitroben-zene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)amino]-4-nitro-benzene, 4-[(2,3-dihydroxypropyl)amino]-3-nitro-1-trifluoromethylbenzene (HC Yellow No. 6), 1-chloro-2,4-bis[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 1,4-di[(2,3-dihydroxypropyl)amino]-9,10-anthraquinone, 1-[(2-hydroxyethyl)amino]-4-methylamino-9,10-anthraquinone (CI 61505, Disperse Blue No. 3), 2-[(2-aminoethyl)amino]-9,10-anthraquinone (HC Orange No. 5), 1-hydroxy-4-[(4-methyl-2-sulfophenyl)-amino]-9,10-anthraquinone, 1-[(3-aminopropyl)amino]-4-methylamino-9,10-anthraquinone (HC Blue No. 8), 1-[(3-aminopropyl)amino]-9,10-anthraquinone (HC Red No. 8), 1,4-diamino-2-meth-oxy-9,10-anthraquinone (CI 62015, Disperse Red No. 11), Solvent Violet No. 26), 1,4-dihydroxy-5,8-bis[2-hydroxyethyl)amino]-9,10-anthraquinone (CI 62500, Disperse Blue No. 7, Solvent Blue No. 69), 9-(dimethylamino)benzo[a]-phenoxazin-7-ium chloride (CI 51175; Basic Blue No. 6), di[4-(diethylamino)phenyl][4-(ethylamino)naphthyl]carbenium chloride (CI 42595; Basic Blue No. 7), 3,7-di(dimethylamino)phenothiazin-5-ium chloride (CI 52015; Basic Blue No. 9), di[4-(dimethylamino)phenyl][4-(phenylamino)naphthyl]carbenium chloride (CI 44045; Basic Blue No. 26), 2-{[4-(ethyl(2-hydroxyethyl)amino)phenyl]azo}-6-methoxy-3-methylbenzothiazolium methylsul-fate (CI 11154; Basic Blue No. 41), 8-amino-2-bromo-5-hydroxy-4-imino-6-{[3-(trimethyl-ammonio)phenyl]amino}-1(4H-naphthalenone chloride (CI 56059; Basic Blue No. 99), bis[4-(dimethylamino)phenyl][4-(methylamino)phenyl]carbenium chloride (CI 42535; Basic Violet No. 1), tris[4-(dimethylamino)phenyl]carbenium chloride (CI 42555; Basic Violet No. 3), 2-[3,6-(diethylamino)dibenzopyranium-9-yl]benzoyl chloride (CI 45170; Basic Violet No. 10), di(4-aminophenyl)(4-amino-3-methylphenyl)carbenium chloride (CI 42510, Basic Violet No. 14), 1,3-bis[(2,4-diamino-5-methylphenyl)azo]-3-methylbenzene (CI 21010; Basic Brown No. 4), 1-[(4-aminophenyl)azo]-7-(trimethylammonio)-2-naphthol chloride (CI 12250; Basic Brown No. 16), 1-[(4-amino-2-nitrophenyl)azo]-7-(trimethylammonio-2-naphthol chloride (Basic Brown No. 17), 1-[(4-amino-3-nitrophenyl)azo]-7-(trimethylammonio)-2-naphthol chloride (CI 12251; Basic Brown No. 17 [sic]), 3,7-diamino-2,8-dimethyl-5-phenylphenazinium chloride (CI 50240; Basic Red No. 2), 1,4-dimethyl-5-{[(4-(dimethylamino)phenyl]azo}-1,2,4-triazolium chloride (CI 11055; Basic Red No. 22), 2-hydroxy-1-[(2-methoxyphenyl)azo]-7-(trimethylammonio)naphthalene chloride (CI 12245; Basic Red No. 76), 2-{2-[(2,4-dimethoxyphenyl)amino]ethenyl}-1,3,3-trimethyl-3H-indol-1-ium chloride (CI 48055; Basic Yellow No. 11), 3-methyl-1-phenyl-4-{[3-(trimethylammonio)phenyl]azo}pyrazol-5-one chloride (CI 12719; Basic Yellow No. 57), bis[4-(diethylamino)phenyl]phenylcarbenium hydrogen sulfate (1:1) (CI 42040; Basic Green No. 1), 1-[di(2-hydroxyethyl)amino]-3-methyl-4-[(4-nitrophenyl)azo]benzene (CI 11210; Disperse Red No. 17), 4-[(4-aminophenyl)azo]-1-[di(2-hydroxyethyl)amino]-3-methylbenzene (HC Yellow No. 7), 2,6-diamino-3-[(pyridin-3-yl)azo]pyridine, 6-hydroxy-5-[(4-sulfophenyl)azo]-2-naphthalenesulfonic acid disodium salt (CI 15985; Food Yellow No. 3; FD&C Yellow No. 6), 2,4-dinitro-1-naphthol-7-sulfonic acid disodium salt (CI 10316; Acid Yellow No. 1; Food Yellow No. 1), 2-(indan-1,3-dion-2-yl)-quinoline-x,x-sulfonic acid (mixture of mono- and disulfonic acid) (CI 47005; D&C Yellow No. 10; Food Yellow No. 13; Acid Yellow No. 3), 5-hydroxy-1-(4-sulfophenyl)-4-[(4-sulfophenyl)azo]-pyrazole-3-carboxylic acid trisodium salt (CI 19140; Food Yellow No. 4; Acid Yellow No. 23), 9-(2-carboxyphenyl)-6-hydroxy-3H-xanthen-3-one (CI 45350; Acid Yellow No. 73; D&C Yellow No. 8), 5-[(2,4-dinitrophenyl)amino]-2-phenylaminobenzenesulfonic acid sodium salt (CI 10385; Acid Orange No. 3), 4-[(2,4-dihydroxyphenyl)azo]benzenesulfonic acid monosodium salt (CI 14270; Acid Orange No. 6), 4-[(2-hydroxynaphth-1-yl)azo]benzenesulfonic acid sodium salt (CI 15510; Acid Orange No. 7), 4-[(2,4-dihydroxy-3-[(2,4-dimethylphenyl)azo]phenyl)azo]benzenesulfonic acid sodium salt (CI 20170; Acid Orange No. 24), 4-hydroxy-3-[(4-sulfonaphth-1-yl)azo]-1-naphthalenesulfonic acid disodium salt (CI 14720; Acid Red No. 14), 6-hydroxy-5-[(4-sulfonaphth-1-yl)azo]-2,4-naphthalenedisulfonic acid trisodium salt (CI 16255; Ponceau 4R; Acid Red No. 18), 3-hydroxy-4-[(4-sulfonaphth-1-yl)azo]-2,7-naphthalenedisulfonic acid trisodium salt (CI 16185; Acid Red No. 27), 8-amino-1-hydroxy-2-(phenylazo)-3,6-naphthalenedisulfonic acid disodium salt (CI 17200; Acid Red No. 33), 5-(acetylamino)-4-hydroxy-3-[(2-methylphenyl)azo]-2,7-naphthalenedisulfonic acid disodium salt (CI 18065; Acid Red No. 35), 2-(3-hydroxy-2,4,5,7-tetraiododibenzopyran-6-on-9-yl)benzoic acid disodium salt (CI 45430; Acid Red No. 51), N-[6-(diethylamino)-9-(2,4-disulfophenyl)-3H-xanthen-3-ylidene]-N-ethylethanammonium hydroxide, inner salt, sodium salt (CI 45100; Acid Red No. 52), 8-{[4-(phenylazo)phenyl]azo}-7-naphthol-1,3-disulfonic acid disodium salt (CI 27290; Acid Red No. 73), 2',4',5',7'-tetrabromo-3',6'-dihydroxyspiro[isobenzofuran-1(3H), 9'-[9H]-xanthen]-3-one disodium salt (CI 45380; Acid Red No. 87), 2',4',5',7'-tetrabromo-4,5,6,7-tetrachloro-3',6'-dihydroxyspiro[isobenzofuran-1(3H), 9'-[9H]-xanthen]-3-one disodium salt (CI 45410; Acid Red No. 92), 3',6'-dihydroxy-4',5'-diiodispiro[isobenzofuran-1(3H), 9'(9H)xanthen]-3-one disodium salt (CI 45425; Acid Red No. 95), (2-sulfophenyl)di[4-(ethyl-((4-sulfophenyl)methyl)amino)phenyl]carbenium disodium salt betaine (CI 42090; Acid Blue No. 9; FD&C Blue No. 1), 1,4-bis[(2-sulfo-4-methylphenyl)amino]-9,10-anthraquinone disodium salt (CI 61570; Acid Green No. 25), bis[4-(dimethylamino)phenyl]-3,7-disulfo-2-hydroxynaphth-1-yl)car-benium inner salt, monosodium salt (CI 44090; Food Green No. 4; Acid Green No. 50), bis[4-(di-ethylamino)phenyl][2,4-disulfophenyl)carbenium inner salt, sodium salt (2:1) (CI 42045; Food Blue No. 3; Acid Blue No. 1), bis[4-(diethylamino)phenyl](5-hydroxy-2,4-disulfophenyl)carbenium inner salt, calcium salt (2:1) (CI 42051; Acid Blue No. 3), 1-amino-4-(cyclohexylamino)-9,10-anthra-quinone-2-sulfonic acid sodium salt (CI 62045; Acid Blue No. 62), 2-(1,3-dihydro-3-keto-5-sulfo-2H-indol-2-ylidene)-2,3-dihydro-3-keto-1H-indole-5-sulfonic acid disodium salt (CI 73015; Acid Blue No. 74), 9-(2-carboxyphenyl)-3-[(2-methylphenyl)amino]-6-[(2-methyl-4-sulfophenyl)amino]-xanthylium inner salt, monosodium salt (CI 45190; Acid Violet No. 9), 1-hydroxy-4-[(4-methyl-2-sulfophenyl)amino]-9,10-anthraquinone sodium salt (CI 60730; D&C Violet No. 2; Acid Violet No. 43), bis{3-nitro-4-[(4-phenylamino)-3-sulfophenylamino]phenyl}sulfone (CI 10410; Acid Brown No. 13), 5-amino-4-hydroxy-6-[(4-nitrophenyl)azo]-3-(phenylazo)-2,7-naphthalenedisulfonic acid diso-dium salt (CI 20470; Acid Black No. 1), 3-hydroxy-4-[(2-hydroxynaphth-1-yl)azo]-7-nitro-1-naph-thalenesulfonic acid chromium complex (3:2) (CI 15711; Acid Black No. 52), 3-[(2,4-dimethyl-5-sulfophenyl)azo]-4-hydroxy-1-naphthalenesulfonic acid disodium salt (CI 14700; Food Red No. 1; FD&C Red No. 4), 4-(acetylamino)-5-hydroxy-6-[(7-sulfo-4-[(4-sulfophenyl)azo]naphth-1-yl)azo]-1,7-naphthalenedisulfonic acid tetrasodium salt (CI 28440; Food Black No. 1) and 3-hydroxy-4-(3-methyl-5-keto-1-phenyl-4,5-dihydro-1H-pyrazol-4-ylazo)naphthalene-1-sulfonic acid sodium salt, chromium complex (Acid Red No. 195), alone or in combination with one another.

Among the aforesaid direct dyes, the following compounds—alone or in combination with one another—are particularly preferred:

hydroxyethyl-2-nitro-p-toluidine, 2-hydroxyethylpicramic acid, 4-nitrophenylaminourea, tri(4-amino-3-methylphenyl)carbenium chloride (Basic Violet 2), 1,4-di-amino-9,10-anthracenedione (Disperse Violet 1), 1-(2-hydroxyethyl)amino-2-nitro-4-[di(2-hydroxy-ethyl)amino] benzene (HC Blue No. 2), 4-[ethyl-(2-hydroxyethyl)amino]-1-[(2-hydroxyethyl)amino]-2-nitrobenzene hydrochloride (HC Blue No. 12), 1-amino-4-[di(2-hydroxyethyl)amino]-2-nitro-benzene hydrochloride (HC Red No. 13), 3-{[2-nitro-4-(trifluoromethyl)phenyl]amino}-1,2-propanediol (HC Yellow No. 6), 4-amino-1[(2-hydroxyethyl)amino]-2-nitrobenzene (HC Red No. 3), 4-amino-3-nitrophenol, 4[(2-hydroxyethyl)amino]-3-nitrophenol, 1-amino-5-chloro-4-[di(2,3-dihydroxypropyl)amino]-2-nitrobenzene (HC Red No. 10, 5-chloro-1,4-[di(2,3-dihydroxypropyl)amino]-2-nitrobenzene (HC Red No. 11), 2-chloro-6-ethylamino-4-nitrophenol, 2-amino-6-chloro-4-nitrophenol, 4-[(2-hydroxyethyl)amino]-3-nitro-1-trifluoromethylbenzene (HC Yellow No. 13), 8-amino-2-bromo-5-hydroxy-4-imino-6-{[3-(trimethylammonio)phenyl]amino}-1(4H)-naphthalenone chloride (CI 56059; Basic Blue No. 99), 1-[(4-aminophenyl)azo]-

7-(trimethylammonio)-2-naphthol chloride (CI 12250; Basic Brown No. 16), 1-[(4-amino-2-nitrophenyl)azo]-7-(trimethylammonio)-2-naphthol chloride (Basic Brown No. 17), 2-hydroxy-1-[(2-methoxyphenyl)azo]-7-(trimethylammonio)naphthalene chloride (CI 12245; Basic Red No, 76), 3-methyl-1-phenyl-4-{[3-(trimethylammonio) phenyl]azo}pyrazol-5-one chloride (CI 12719; Basic Yellow No. 570 and 2,6-diamino-3-[(pyridin-3-yl)azo]pyridine and the salts thereof.

The total amount of direct dyes in the agent of the invention is about 0.01 to 7 weight percent and preferably about 0.2 to 4 weight percent. Particularly preferred dyes are listed in Table 1.

Other known and common dyes that can be contained in the coloring agent of the invention are described in, among other publications, E. Sagarin "Cosmetics, Science and Technology", Interscience Publishers Inc., New York (1957), pages 503 ff, in H. Janistyn "Handbuch der Kosmetika und Riechstoffe" [Handbook of Cosmetics and Perfumes], vol. 3 (1973), pages 388 ff, and in K. Schrader "Grundlagen und Rezepturen der Kosmetika" [Fundamentals and Formulations of Cosmetics], 2nd edition (1989), pages 782-815, which in particular are included herein by reference.

In addition, the agent of the invention can contain antioxidants, for example ascorbic acid, thioglycolic acid or sodium sulfite, as well as complexing agents for heavy metals, for example an ethylenediamine tetraacetate, or nitriloacetic acid, in an amount of up to about 0.5 weight percent. The colorant carrier composition can contain perfume oils in an amount of up to about 1 weight percent. Naturally, the afore-described hair colorant can optionally contain other additives commonly employed in hair colorants, such as, for example, thickeners, for example homopolymers of acrylic acid, vegetable gums, cellulose derivatives and starch derivatives, algal polysaccharides, amphiphilic associative thickeners, furthermore preservatives; complexing agents, solvents such as water, lower aliphatic alcohols, for example aliphatic alcohols with 1 to 4 carbon atoms, such as ethanol, propanol, and isopropanol, or glycols such as glycerol and 1,2-propylene glycol, wetting agents or emulsifiers from the classes of anionic, cationic, amphoteric or nonionic surfactants; furthermore softeners; vaselines; silicone oils, paraffin oil, polysorbates and fatty acids as well as hair-care agents such as cationic polymers or resins, lanolin derivatives, cholesterol, vitamins, pantothenic acid and betaine. The said constituents are used in amounts usually employed for such purposes, for example the wetting agents and emulsifiers at a concentration from 0.1 to 30 weight percent and the hair-care agents at a concentration from 0.1 to 5.0 weight percent.

The pH of the colorant of the invention is in the range of about 5 to 11 and preferably 7 to 9.

Depending on the composition and the desired pH of the colorant, the pH is preferably adjusted with an organic amine, for example a glucamine, aminomethylpropanol, monoethanolamine or triethanolamine, but ammonia or an inorganic base, for example sodium hydroxide, potassium hydroxide, sodium carbonate or calcium hydroxide, or an organic acid or inorganic acid, such as, for example, lactic acid, citric acid, acetic acid or phosphoric acid, can also be used. The agent of the invention is applied to dry or previously washed fibers and after an exposure time of 5 to 60 minutes and preferably after 10 to 45 minutes it is rinsed out with water and optionally washed out with a shampoo. The keratin fibers can then optionally be post-treated in the usual manner and dried.

Another object is the use of an aqueous or aqueous-alcoholic preparation containing a combination of oxidation dyes and direct dyes, wherein there are present at least three direct dyes and the quantitative ratio of oxidation dyes to direct dyes equals 5:1 to 0.5:1, for the preparation of an agent for coloring keratin fibers, said agent being free of chemical oxidants and upon air oxidation (namely without the addition of a chemical oxidant) gives a uniform and stable coloration immediately after use.

The following examples will explain in greater detail the object of the invention without limiting it to the examples:

EXAMPLES

Example 1

| Aerosol Colorant in Cream Form | |
|---|---|
| 1.2 g | of cetylstearyl alcohol |
| 0.6 g | of sodium laurylsulfate |
| 0.1 g | of disodium ethylenediaminetetraacetate |
| 0.2 g | of ascorbic acid |
| 2.5 g | of 1,2-propylene glycol |
| 2.5 g | of ethanol |
| 4.5 g | of ammonia |
| 2.5 g | of monoethanolamine |
| 1.3 g | of 2,5-diaminotoluene sulfate |
| 0.7 g | of 5-amino-2-methylphenol |
| 1.3 g | of 2,2'-((4-((2-hydroxyethyl)amino]imino-3-nitrophenyl)}bis-ethanol (HC Blue No. 2) |
| 0.5 g | of 2-[(4-amino-2-nitrophenyl)amino)-3-nitrophenyl)imino)ethanol (HC Red No. 3) |
| 0.6 g | of 3-(4-amino-2-chloro-5-nitrophenyl)amino-1,2-propanediol (HC Red No. 10 + 11) |
| 0.3 g | of perfume oil |
| to 100.0 g | water |

The dye compositions prepared by the hot emulsification method were introduced into appropriate compressed-gas containers with propane/butane and F 152 (1:1 ratio) in an active ingredient/propellant gas ratio of 95:5%.

The aerosol foam was applied to dry hair and after an exposure time of 20 minutes rinsed out with water. The hair was then dried. This gave a lustrous red-brown coloration.

Example 2

| Aerosol Colorant in Gel Form | |
|---|---|
| 2.00 g | of hydroxyethylcellulose |
| 20.00 g | of cocamidopropylbetaine |
| 1.50 g | of D-panthenol |
| 10.00 g | of ethanol |
| 0.10 g | of disodium tetraborate |
| 0.10 g | of disodium ethylenediaminetetraacetate |
| 0.20 g | of ascorbic acid |
| 4.50 g | of monoethanolamine |
| 2.00 g | of 2,5-diaminotoluene sulfate |
| 0.75 g | of resorcinol |
| 0.70 g | of 2-amino-4-(2'-hydroxyethylamino)anisole |
| 0.35 g | of 3-aminophenol |
| 3.10 g | of (4-ethyl((2-hydroxyethyl)amino)-2-nitrophenyl)amino}ethanol hydrochloride (HC Blue No. 12) |
| 1.00 g | of 3-{[2-nitro-4-(trifluoromethyl)phenyl]amino}-1,2-propanediol (HC Yellow No. 6) |
| 1.00 g | of 3-[(4,5-dihydro-3-methyl-5-keto-1-phenyl-1H-pyrazol-4-yl)azo]-N,N,N-trimethylbenzenaminium chloride (Basic Yellow No. 57) |
| 0.47 g | of 1,4-diamino-9,10-anthracenedione (Disperse Violet No. 1) |
| 0.70 g | of 1-N-hydroxyethylamino-4-methyl-2-nitrobenzene |
| 3.10 g | of sodium hydroxide, 20% aqueous solution |
| 0.50 g | of perfume oil |
| to 100.00 g | water |

The gel base prepared by the cold-mixing method was combined with hot-dissolved dyes and introduced into an appropriate compressed-gas container with propane/butane and F 152 (1:1 ratio) in an active ingredient/propellant gas ratio of 95:5%.

The aerosol foam was applied to washed hair and after an exposure time of 15 minutes rinsed out with water. The hair was then washed with a gentle shampoo, again rinsed with water and then dried. This gave a lustrous dark-brown coloration.

Example 3

| | Cationic Aerosol Colorant in Gel Form |
|---|---|
| 1.300 g | hydroxyethylcellulose |
| 6.000 g | of cocamidopropylbetaine |
| 2.000 g | of polyethylene glycol 300 capryl glyceride (Softigen ® 767) |
| 3.000 g | of decyl glucoside (Plantaren ® 2000) |
| 1.000 g | of cetyltrimethylammonium chloride |
| 5.000 g | of isopropanol |
| 0.200 g | of ascorbic acid |
| 0.100 g | of disodium ethylenediaminetetraacetate |
| 2.000 g | of 2,5-diaminotoluene sulfate |
| 0.750 g | of resorcinol |
| 0.700 g | of 2-amino-4-(2'-hydroxyethylamino)anisole |
| 0.350 g | of 3-aminophenol |
| 5.800 g | of monoethanolamine |
| 0.300 g | of ((4-ethyl((2-hydroxyethyl)amino)-2-nitrophenyl)amino)ethanol hydrochloride (HC Blue No. 12) |
| 1.000 g | of 2,2'-((4-((2-hydroxyethyl)amino)-3-nitrophenyl)imino)bis-ethanol (HC Blue No. 2) |
| 0.400 g | of 3-{[2-nitro-4-(trifluoromethyl)phenyl]amino}-1,2-propanediol (HC Yellow No. 6) |
| 0.013 g | of 2,6-diamino-3-[(pyridin-3-yl)azo]pyridine |
| 0.170 g | of 3-hydroxy-4-[(2-hydroxy-1-naphthalenyl)azo]-7-nitro-1-naphthalene-sulfonic acid monosodium salt (Acid Black No. 52) |
| 0.066 g | of 3-(4-amino-2-chloro-5-nitrophenyl)amino-1,2-propanediol (HC Red No. 10 + 11) |
| 0.500 g | of perfume oil |
| to 100.000 g | water |

The gel base prepared by the cold-mixing method was combined with the hot-dissolved dyes and introduced into an appropriate compressed-gas container with propane/butane and F 152 (1:1 ratio) in an active ingredient/gas propellant ratio of 95:5%. The aerosol foam was applied to dry hair and after an exposure time of 30 minutes rinsed out with water. The hair was then dried. This gave a lustrous black coloration.

Example 4

| | Liquid Air Oxidation Colorant |
|---|---|
| 2.50 g | of oleic acid |
| 2.00 g | of cetearyl alcohol |
| 4.00 g | of Undeceth-3 |
| 5.00 g | of ethanol |
| 2.50 g | of aminomethylpropanol |
| 0.43 g | of 2,5-diaminotoluene sulfate |
| 0.47 g | of resorcinol |
| 0.31 g | of 2-methylresorcinol |
| 1.59 g | of 4-amino-3-methylphenol |
| 1.01 g | of 5-amino-2-methylphenol |
| 0.30 g | of 2,2'-((4-((2-hydroxyethyl)amino)-3-nitrophenyl)imino)bis-ethanol (HC Blue No. 2) |

| | -continued |
|---|---|
| | Liquid Air Oxidation Colorant |
| 0.30 g | of 3-(4-amino-2-chloro-5-nitrophenyl)amino-1,2-propanediol (HC Red No. 10 + 11) |
| 0.20 g | of 2-amino-6-chloro-4-nitrophenol |
| to 100.00 g | water |

The colorant was applied to dry hair and after an exposure time of 20 minutes rinsed out with water. The hair was then dried. This gave a lustrous garnet-red coloration.

Unless otherwise indicated, all percentages are by weight.

We claim:

1. An aqueous or aqueous-alcoholic agent for coloring keratin fibers, said aqueous-alcoholic agent comprising a combination oxidation dyes and at least three direct dyes; wherein a quantitative ratio of said oxidation dyes to said direct dyes is from 5:1 to 0.5:1 and said dye-containing preparation is free of chemical oxidants.

2. The agent as defined in claim 1, wherein said oxidation dyes are each selected from the group consisting of 2,5-diaminotoluene, 2,4-diaminophenoxyethanol, resorcinol, 2-methylresorcinol, m-aminophenol, 4-amino-3-methylphenol, 4-amino-2-hydroxytoluene, 6-amino-3-methylphenol, 2-amino-4-hydroxyethylaminoanisole, 1-naphthol, hydroxyethyl-3,4-methylenedioxyaniline, 2,5-diaminophenylethanol, N,N-bis(2-hydroxyethyl)-p-phenylenediamine, phenylmethylpyrazolone, 1-hydroxyethyl-4,5-diaminopyrazole, and salts thereof.

3. The agent as defined in claim 1, wherein said at least three direct dyes are each selected from the group consisting of hydroxyethyl-2-nitro-p-toluidine, 2-hydroxyethylpicramic acid, 4-nitrophenylaminourea, Basic Violet 2, Disperse Violet 1, HC Blue No. 2, HC Blue No. 12, HC Red No. 13, HC Yellow No. 6, HC Red No. 3,4-amino-3-nitrophenol, 4-[(2-hydroxyethyl)amino]-3-nitrophenol, HC Red No. 10, HC Red No. 11, 2-chloro-6-ethylamino-4-nitrophenol, 2-amino-6-chloro-4-nitrophenol, HC Yellow, No. 13, Basic Blue No. 99, Basic Brown No. 16, Basic Brown No. 17, Basic Red No. 76, Basic Yellow No. 57, 2,6-diamino-3-[(pyridin-3-yl)-azo]-pyridine and salts thereof.

4. The agent as defined in claim 1, wherein the agent further comprises at least one alcohol selected from the group consisting of ethanol, isopropanol, n-propanol, glycerol, and 1,2-polyethylene glycol.

5. The agent as defined in claim 1, consisting of a hair colorant.

6. A method for coloring keratin fibers, said method comprising the steps of:
a) providing an aqueous or aqueous-alcoholic dye-containing preparation comprising a combination oxidation dyes and at least three direct dyes, in which a quantitative ratio of said oxidation dyes to said direct dyes is from 5:1 to 0.5:1, said dye-containing preparation being free of chemical oxidants;
b) applying said aqueous or aqueous-alcoholic dye-containing preparation of step a) to the keratin fibers;
c) after applying of step b), allowing said aqueous or aqueous-alcoholic dye-containing preparation to act on the keratin fibers for an exposure time of from 5 to 60 minutes; and
d) after the exposure time of step c), rinsing said aqueous or aqueous-alcoholic dye-containing preparation from the keratin fibers with water and then drying the keratin fibers;

said method being performed without addition of any said chemical oxidants.

7. The method as defined in claim 6, further comprising washing the keratin fibers with a shampoo and then rinsing with said water before the keratin fibers are dried.

8. The method as defined in claim 6, wherein air oxidation of said oxidation dyes occurs while said aqueous-alcoholic dye-containing preparation acts on the keratin fibers.

9. The method as defined in claim 6, wherein said keratin fibers consist of hair.

10. The method as defined in claim 6, wherein said oxidation dyes are each selected from the group consisting of 2,5-diaminotoluene, 2,4-diaminophenoxyethanol, resorcinol, 2-methylresorcinol, m-aminophenol, 4-amino-3-methylphenol, 4-amino-2-hydroxytoluene, 6-amino-3-methylphenol, 2-amino-4-hydroxyethylaminoanisole, 1-naphthol, hydroxyethyl-3,4-methylenedioxyaniline, 2,5-diaminophenylethanol, N,N-bis(2-hydroxyethyl)-p-phenylenediamine, phenylmethylpyrazolone, 1-hydroxyethyl-4,5-diaminopyrazole and salts thereof.

11. The method as defined in claim 6, wherein said at least three direct dyes are each selected from the group consisting of hydroxyethyl-2-nitro-p-toluidine, 2-hydroxyethylpicramic acid, 4-nitrophenylaminourea, Basic Violet 2, Disperse Violet 1, HC Blue No. 2, HC Blue No. 12, HC Red No. 13, HC Yellow No. 6, HC Red No. 3,4-amino-3-nitrophenol, 4-[(2-hydroxyethyl)amino]-3-nitrophenol, HC Red No. 10, HC Red No. 11, 2-chloro-6-ethylamino-4-nitrophenol, 2-amino-6-chloro-4-nitrophenol, HC Yellow, No. 13, Basic Blue No. 99, Basic Brown No. 16, Basic Brown No. 17, Basic Red No. 76, Basic Yellow No. 57, 2,6-diamino-3-[(pyridin-3-yl)-azo]-pyridine and salts thereof.

12. The method as defined in claim 6, wherein said dye-containing preparation comprises at least one alcohol selected from the group consisting of ethanol, isopropanol, n-propanol, glycerol and 1,2-polyethylene glycol.

13. A process of preparing an aqueous or aqueous-alcoholic dye-containing preparation for coloring keratin fibers, said process comprising adding a combination of oxidation dyes and at least three direct dyes to an aqueous or aqueous-alcoholic composition that is free of chemical oxidants so as to form said aqueous or aqueous-alcoholic dye-containing preparation for coloring the keratin fibers that does not contain any chemical oxidants;
wherein a quantitative ratio of said oxidation dyes to said direct dyes in said aqueous or aqueous-alcoholic dye-containing preparation is from 5:1 to 05:1 and wherein said aqueous or aqueous-alcoholic dye-containing preparation is free of chemical oxidants.

14. The process as defined in claim 13, wherein said aqueous or aqueous-alcoholic preparation contains at least one alcohol selected from the group consisting of ethanol, isopropanol, n-propanol, glycerol and 1,2-polyethylene glycol.

15. An aqueous or aqueous-alcoholic agent for coloring keratin fibers, said agent comprising a combination of oxidation dyes and at least three direct dyes;
wherein said oxidation dyes are each selected from the group consisting of 2,5-diaminotoluene, 2,4-diaminophenoxyethanol, resorcinol, 2-methylresorcinol, m-aminophenol, 4-amino-3-methylphenol, 4-amino-2-hydroxytoluene, 6-amino-3-methylphenol, 2-amino-4-hydroxyethylaminoanisole, 1-naphthol, hydroxyethyl-3,4-methylenedioxyaniline, 2,5-diaminophenylethanol, N,N-bis(2-hydroxyethyl)-p-phenylenediamine, phenylmethylpyrazolone, 1-hydroxyethyl-4,5-diaminopyrazole and salts thereof; and
wherein said at least three direct dyes are each selected from the group consisting of hydroxyethyl-2-nitro-p-toluidine, 2-hydroxyethylpicramic acid, 4-nitrophenylaminourea, Basic Violet 2, Disperse Violet 1, HC Blue No. 2, HC Blue No. 12, HC Red No. 13, HC Yellow No. 6, HC Red No. 3,4-amino-3-nitrophenol, 4-[(2-hydroxyethyl)amino]-3-nitrophenol, HC Red No. 10, HC Red No. 11, 2-chloro-6-ethylamino-4-nitrophenol, 2-amino-6-chloro-4-nitrophenol, HC Yellow, No. 13, Basic Blue No. 99, Basic Brown No. 16, Basic Brown No 17, Basic Red No. 76, Basic Yellow No. 57, 2,6-diamino-3-[(pyridin-3-yl)-azo]-pyridine, and salts thereof; and
wherein a quantitative ratio of said oxidation dyes to said direct dyes is from 5:1 to 0.5:1 and said dye-containing preparation is free of chemical oxidants.

16. A method of coloring keratin fibers, said method said method comprising the steps of:
a) providing an aqueous or aqueous-alcoholic dye-containing preparation, said dye-containing preparation comprising a combination of oxidation dyes and at least three direct dyes, in which a quantitative ratio of said oxidation dyes to said direct dyes is from 5:1 to 0.5:1, said dye-containing preparation being free of chemical oxidants;
b) applying said aqueous or aqueous-alcoholic dye-containing preparation of step a) to the keratin fibers;
c) after applying of step b), allowing said aqueous or aqueous-alcoholic dye-containing preparation to act on the keratin fibers for an exposure time of from 5 to 60 minutes; and
d) after the exposure time of step c), rinsing said aqueous or aqueous-alcoholic dye-containing preparation from the keratin fibers with water and then drying the keratin fibers;
wherein said method is performed without addition of any of said chemical oxidants;
wherein said oxidation dyes are each selected from the group consisting of 2,5-diaminotoluene, 2,4-diaminophenoxyethanol, resorcinol, 2-methylresorcinol, m-aminophenol, 4-amino-3-methylphenol, 4-amino-2-hydroxytoluene, 6-amino-3-methylphenol, 2-amino-4-hydroxyethylaminoanisole, 1-naphthol, hydroxyethyl-3,4-methylenedioxyaniline, 2,5-diaminophenylethanol, N,N-bis(2-hydroxyethyl)-p-phenylenediamine, phenylmethylpyrazolone, 1-hydroxyethyl-4,5-diaminopyrazole, and salts thereof; and
wherein said at least three direct dyes are each selected from the group consisting of hydroxyethyl-2-nitro-p-toluidine 2-hydroxyethylpicramic acid, 4-nitrophenylaminourea, Basic Violet 2, Disperse Violet 1, HC Blue No. 2, HC Blue No. 12, HC Red No. 13, HC Yellow No. 6, HC Red No. 3,4-amino-3-nitrophenol, 4-[(2-hydroxyethyl)amino]-3-nitrophenol, HC Red No. 10, HC Red No. 11, 2-chloro-6-ethylamino-4-nitrophenol, 2-amino-6-chloro-4-nitrophenol, HC Yellow, No. 13, Basic Blue No. 99, Basic Brown No. 16, Basic Brown No. 17, Basic Red No. 76, Basic Yellow No. 57, 2,6-diamino-3-[(pyridin-3-yl)-azo]-pyridine, and salts thereof.

* * * * *